United States Patent [19]

Bays et al.

[11] 4,399,294

[45] Aug. 16, 1983

[54] PROCESS FOR THE PREPARATION OF A FURAN DERIVATIVE

[75] Inventors: David E. Bays, Ware; John W. Clitherow, Sawbridgeworth; Duncan B. Judd, Ware, all of England

[73] Assignee: Glaxo Group Limited, London, England

[21] Appl. No.: 335,686

[22] Filed: Dec. 30, 1981

[30] Foreign Application Priority Data

Dec. 30, 1980 [GB] United Kingdom ................ 8041493

[51] Int. Cl.³ ............................................ C07D 307/46
[52] U.S. Cl. ..................................... 549/495; 549/370; 549/448; 549/488; 549/491
[58] Field of Search ................................ 549/488, 495

[56] References Cited

U.S. PATENT DOCUMENTS 4,128,658 12/1978 Price et al. ........................... 424/285
4,318,913 3/1982 Clitherow et al. .................. 424/267

OTHER PUBLICATIONS

Patai, ed., The Chemistry of the Carbonyl Group, Interscience Publishers, New York, 1966, pp. 188–192.

*Primary Examiner*—Richard Raymond
*Attorney, Agent, or Firm*—Bacon & Thomas

[57] ABSTRACT

Ranitidine is prepared by treating an aldehyde of formula (II)

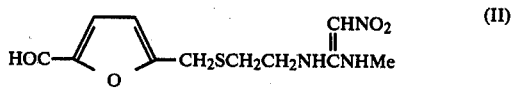

with dimethylamine and a reducing agent which is capable of effecting reductive alkylation to introduce the group $Me_2NCH_2-$ but which does not reduce the nitroethene group. The reaction is carried out in a suitable solvent, preferably in the presence of an acid or followed by treatment with an acid. Suitable reducing agents include, diborane, aluminium hydride and alkali or alkaline earth metal borohydrides.

The aldehyde (II) may be generated in situ from an acetal of formula (III)

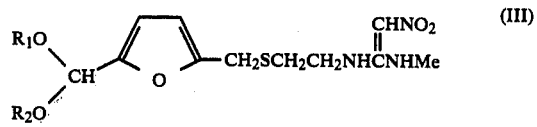

where $R_1$ and $R_2$ are both alkyl groups or $R_1OCHOR_2$ forms a cyclic acetal.

10 Claims, No Drawings

PROCESS FOR THE PREPARATION OF A FURAN DERIVATIVE

This invention relates to a process for the preparation of a furan derivative.

The furan derivative of formula (I)

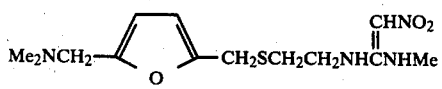

which is known as ranitidine is disclosed in British Patent Specification No. 1,565,966 as a potent and selective H$_2$-antagonist.

The present invention provides a process for the preparation of ranitidine of formula (I) which comprises treating an aldehyde of formula (II)

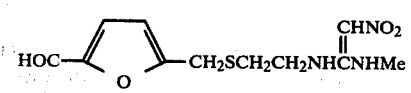

with dimethylamine and a reducing agent which is capable of effecting reductive alkylation to introduce the dimethylaminomethyl group (Me$_2$NCH$_2$—) but which does not reduce the nitroethene group, the reaction being carried out in a suitable solvent.

Suitable reducing agents include hydride reducing agents such as diborane, aluminium hydride or an alkali or alkaline earth metal borohydride e.g. sodium or calcium borohydride or sodium cyanoborohydride, of which sodium borohydride and sodium cyanoborohydride are preferred.

The above reaction is carried out in a suitable solvent such as an aqueous alkanol (e.g. ethanol or methanol), aqueous dioxan or aqueous tetrahydrofuran, and at a suitable temperature for example within the range 10° to 100° C. and conveniently at 50°–100° C.

Optionally the reaction may be carried out in the presence of an acid such as an organic carboxylic acid (e.g. acetic acid), or the reaction with the reducing agent may be followed by treatment with an acid for example an inorganic acid such as hydrochloric acid or an organic acid such as acetic acid.

The aldehyde of formula (II) is preferably generated in situ from a suitable precursor such as an acetal of formula (III)

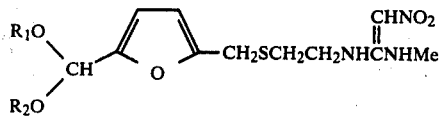

in which R$_1$ and R$_2$ are alkyl groups (e.g. methyl or ethyl), or the group R$_1$OCHOR$_2$ forms a cyclic acetal (e.g. 1,3-dioxolan-2-yl or 1,3-dioxan-2-yl).

Thus for example an acetal of formula (III) may be hydrolysed using either an inorganic acid e.g. 2 N hydrochloric acid or an organic acid e.g. formic acid, preferably in the presence of an excess of an acid addition salt of dimethylamine (e.g. dimethylamine hydrochloride). Reduction is then effected as described above, optionally after the addition of dimethylamine.

In the above process it is convenient to use an acetal of formula (III) in which R$_1$OCHOR$_2$ is a cyclic acetal group, more particularly 1,3-dioxolan-2-yl.

Compounds of formula (III) in which R$_1$ and R$_2$ are both C$_{1-4}$ alkyl groups (e.g. methyl or ethyl) or the group R$_1$OCHOR$_2$ forms a 5- or 6-membered cyclic acetal (i.e. 1,3-dioxolan-2-yl or 1,3-dioxan-2-yl) form a further aspect of the present invention.

The intermediate acetal of formula (III) may be prepared from the amine of the formula (IV)

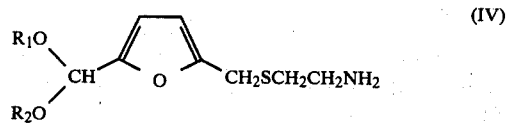

by reaction with a compound of formula (V)

where L is a leaving group such as alkylthio (e.g. methylthio). The reactants may for example be heated in vacuo e.g. at 100° C.

The amine of formula (IV) may be prepared from a compound of formula (VI)

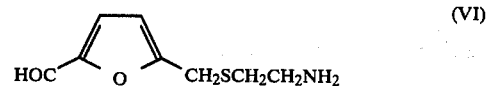

in which the amino group is protected, for example as a phthalimide group. The aldehyde group in the compound of formula (VI) is then converted into an acetal group as in compound (IV) by reaction with an appropriate alcohol (e.g. methanol) or diol (e.g. ethylene glycol). The reaction is carried out in the presence of a catalyst (e.g. p-toluenesulphonic acid), in a solvent such as benzene, at reflux temperature using for example a Dean and Starke apparatus to remove the water generated in the reaction. The phthalimide protecting group may then be removed by treatment with for example, methylamine, and the resulting amine of formula (IV) may conveniently be isolated as an acid addition salt such as an oxalate.

The compound of formula (VI) in which the amino group is protected may be prepared from the amine of formula (VII)

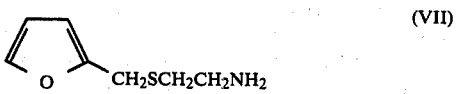

(in which the amino group is again protected as for example a phthalimide group) by formylation using for example phosphoryl chloride in dimethylformamide at room temperature.

The invention is illustrated by the following Examples:

EXAMPLE 1

N-[2-[[5-[(Dimethylamino)methyl]-2-furanylmethyl]thio]ethyl]N'-methyl-2-nitro-1,1-ethenediamine

1.
N-[2-[(5-Formyl-2-furanylmethyl)thio]ethyl]-1H-isoindole-1,3 (2H)-dione

A solution of phosphoryl chloride (21.4 g) in dry dimethylformamide (40 ml), cooled in ice, was added portionwise to a solution of N-[2-[(2-furanylmethyl)thio]ethyl]-1H-isoindole-1,3(2H)-dione (21.4 g) in dry dimethylformamide (70 ml). After 5 hours at room temperature, the solution was poured into iced water (1.7 l). Isopropyl alcohol (150 ml) was added and after 18 hours the solid which separated was filtered and crystallised from ethyl acetate-ether to give the title compound (22.3 g) m.p. 76°-77°.

2.
2-[2-[[5-(1,3-Dioxolan-2-yl)-2-furanylmethyl]thio]ethyl-]isoindole-1,3-(2H)-dione A mixture of N-[2-[(5-formyl-2-furanylmethyl)thio]ethyl ]-1H-isoindole-1,3-(2H)-dione (15 g), p-toluenesulphonic acid (0.12 g) and 1,2-ethanediol (6.2 g) in benzene (160 ml) was refluxed under Dean-Starke conditions. After 6 hours, the solution was washed with a solution of sodium carbonate (1.2 g) in water (25 ml), dried (Na$_2$CO$_3$), decolourised (charcoal) and evaporated in vacuo. The semi-solid residue was suspended in ether (200 ml) and filtered off to give the title compound (13.5 g), m.p. 83°-85°.

3.
2-[[5-(1,3-Dioxolan-2-yl)-2-furanylmethyl]thio]ethanamine oxalate (1:1)

2-[2-[[5-(1,3-Dioxolan-2-yl)-2-furanylmethyl]thio]ethyl]isoindole-1,3-(2H)-dione (12.88 g) was dissolved in a mixture of ethanol (50 ml) and methylamine (33% in ethanol) (20.4 ml). After 1 hour, the solution was evaporated in vacuo and the residue suspended in ether, triturated and filtered. Evaporation of the filtrate gave an oily residue (5.5 g) which was dissolved in tetrahydrofuran (40 ml) and treated with a solution of oxalic acid (3.12 g) in tetrahydrofuran (30 ml). The solid which separated was filtered off to give the title compound (6.65 g) m.p. 86°-89° (decomp.)

4.
N-[2-[[5-(1,3-Dioxolan-2-yl)-2-furanylmethyl]thio]ethyl]-N'-methyl-2-nitro-1,1-ethenediamine 2-[[5-(1,3-Dioxolan-2-yl)-2-furanylmethyl]thio]ethanamine oxalate (1:1) (6.0 g) was added to a solution of sodium carbonate (6 g) in water (20 ml). The suspension was evaporated in vacuo and the residue suspended in ethyl acetate (100 ml). An excess of anhydrous sodium carbonate was added and the suspension refluxed for 30 mins. After 2 hours, the suspension was filtered and the filtrate evaporated in vacuo to give an oil (4.23 g) to which was added N-methyl-(1-methylthio)-2-nitroethenamine (3 g). The mixture was heated at 98°-100° in vacuo for 1.5 hours and the oily residue chromatographed (silica/acetone). The appropriate eluate was evaporated to give the title compound (5.1 g) as a brown oil.

N.m.r. (CDCl$_3$) τ −0.3, brs (1H); 3.1-3.5, brs, 3.38, s, 3.57, d, 3.78, d, (4H); 4.12, s, (1H); 5.7-6.1, m, (4H); 6.23, s, (2H); 6.60, brm, (2H); 7.10, brm, 7.22, brm, (5H).

5.
N-[2-[[5-[(Dimethylamino)methyl]-2-furanylmethyl]thio]ethyl]-N'-methyl-2-nitro-1,1-ethenediamine To a solution of N-[2-[[5-(1,3-dioxolan-2-yl)-2-furanylmethyl]thio]ethyl]-N'-methyl-2-nitro-1,1-ethenediamine (2.21 g) and dimethylamine hydrochloride (20 g) in water (5 ml) was added 2 N hydrochloric acid (5 ml). After 10 min, dimethylamine (33% in ethanol) (2 ml) was added, the solution cooled to 18° and sodium borohydride (1 g) added portionwise. The suspension was acidified with acetic acid (2.5 ml) and after 15 mins was heated at 60° for 15 mins. The suspension was evaporated to low bulk and an excess of anhydrous sodium carbonate and tetrahydrofuran (100 ml) added. The suspension was refluxed for 2 hours and after 2 hours at room temperature was filtered and the filtrate evaporated in vacuo. The oily residue was chromatographed (silica/methanol) and the appropriate eluate evaporated in vacuo to give the title compound (0.45 g) which was crystallised from methyl isobutyl ketone, m.p. 64°-67°.

A further crystallisation from methyl isobutyl ketone gave the title compound (0.13 g) with m.p. raised to 66°-68°, which was not depressed on admixture with a sample prepared according to the method of Example 15 in British Patent Specification No. 1,565,966. Evaporation of the mother liquor in vacuo gave an oil (0.36 g) also consisting of the title compound.

Nmr (CDCl$_3$): −0.27, br.s, (1H); 3.00, br.s, (1H); 3.40, s, (1H); 3.84, s, (2H); 6.28, s, (2H); 6.42-6.89, s & m, (4H); 6.90-7.43, m, (5H), 7.72, s, (6H).

EXAMPLE 2

N-[2-[[5-[(Dimethylamino)methyl]-2-furanylmethyl]thio]ethyl]-N'-methyl-2-nitro-1,1-ethenediamine To a stirred solution of N-[2-[[5-(1,3-dioxolan-2-yl)-2-furanylmethyl]thio]ethyl]-N'-methyl-2-nitro-1,1-ethenediamine (0.12 g) in tetrahydrofuran (1 ml) at room temperature was added 2 N hydrochloric acid (0.4 ml). After 20 min., a mixture of dimethylamine in ethanol (33%) (1 ml) and acetic acid (5 ml), evaporated to remove the ethanol, was added. The mixture was allowed to stand at room temperature for 20 min., then cooled in an ice bath. To the stirred solution was added sodium borohydride (0.4 g) portionwise during 5 min. After 10 min, acetic acid (1 ml) was added and the solution heated on a steam bath for 15 min. Tetrahydrofuran (30 ml) and excess of sodium carbonate were added and the mixture heated to boiling then cooled to room temperature. After 1 h, the mixture was filtered and the combined filtrate and washings evaporated in vacuo to give an oily residue which was extracted with hot ethyl acetate (25 ml). The extract was evaporated in vacuo to give an oily residue consisting of the title compound (0.06 g).

Tlc; methanol:0.88 ammonia (79:1), R$_f$ 0.45.

EXAMPLE 3

N-[2-[[5-[(Dimethylamino)methyl]-2-furanylmethyl]thio]ethyl]-N'-methyl-2-nitro-1,1-ethenediamine To a stirred solution of N-[2-[[5-(1,3-dioxolan-2-yl)-2-furanylmethyl]thio]ethyl]-N'-methyl-2-nitro-1,1-ethenediamine (1.65 g) and dimethylamine hydrochloride (16.3 g) in water (3.74 ml) and ethanol (6.2 ml) was added 2 N hydrochloric acid (3.74 ml). After 15 min. at room temperature, a solution of dimethylamine in water (40%) (0.85 ml) was added followed by a solution of sodium cyanoborohydride (0.156 g) in water (1 ml). After 1h, the solution was evaporated in vacuo and to the oily residue was added acetic acid (0.5 ml). After 10 min., tetrahydrofuran (100 ml) and an excess of anhydrous sodium carbonate were added, the mixture heated to boiling and allowed to cool to room temperature. After standing for 3 h, the mixture was filtered and the combined filtrate and washings evaporated to low bulk in vacuo. Decolourising charcoal was added to the hot solution and after 1h, the mixture was filtered. The filtrate was evaporated to give an oil (1.7 g) which was chromatographed on silica using methanol:0.88 ammonia (79:1) to give an oil which was dissolved in ethanol. The solution was filtered and evaporated to give an oil (0.75 g) which was crystallised from methyl isobutyl ketone to yield the title compound (0.27 g), m.p. 68°–69.5° which was not depressed on admixture with a sample prepared according to the method of Example 15 in British Patent Specification No. 1,565,966.

EXAMPLE 4

N-[2-[[5-[(Dimethylamino)methyl]-2-furanylmethyl]thio]ethyl]-N'-methyl-2-nitro-1,1-ethenediamine A mixture of N-[2-[[5-(1,3-dioxolan-2-yl)-2-furanylmethyl]thio]ethyl]-N'-methyl-2-nitro-1,1-ethenediamine (3.33 g) and dimethylamine hydrochloride (33 g) in water (3.56 ml), ethanol (12.5 ml) and 2 N hydrochloric acid (7.56 ml) was kept at room temperature for 15 min. A solution of dimethylamine in water (40%) (1.17 ml) was added followed by a solution of sodium cyanoborohydride (0.316 g) in water (1 ml) and the mixture stirred at room temperature for 18h. The mixture was evaporated in vacuo and acetic acid (1 ml) and water (15 ml) added to the residue. Anhydrous sodium carbonate (30 g) was added and the mixture evaporated to dryness in vacuo. To the residue was added tetrahydrofuran (150 ml) and excess of anhydrous sodium carbonate and the mixture heated at boiling for 20 min. The mixture was cooled to room temperature and after 3h was filtered and the filtrate evaporated to give an oil (4.43 g). This was chromatographed on silica using methylene dichloride:ethanol:0.88 ammonia (70:8:1) to give an oil (1.56 g) which was suspended in hot isopropyl acetate (20 ml) and the suspension filtered through diatomaceous earth (Hy-flo). The filtrate was evaporated to dryness in vacuo to give an oil which was crystallised from methyl isobutyl ketone to yield the title compound (0.475 g), m.p. 66°–68.5° which was not depressed on admixture with a sample prepared according to the method of Example 15 in British Patent Specification No. 1,565,966. A further yield of the title compound (0.087 g), m.p. 65°–67° which was not depressed on admixture with a sample prepared according to the method of Example 15 in British Patent Specification No. 1,565,966 was obtained from the crystallisation liquors. The evaporation of the crystallisation liquors in vacuo yielded a viscous oil also consisting of the title compound (0.53 g).

Nmr (CDCl$_3$): 0-–0.5 br.; 3.40, s, (1H); 3.86, s, (2H); 6.27, s, (2H); 6.50–6.84, s & m, (4H); 7.07, br.s, 7.24, m, (5H); 7.73, s, (6H).

EXAMPLE 5

N-[2-[[5-[(Dimethylamino)methyl]-2-furanylmethyl]thio]ethyl]-N'-methyl-2-nitro-1,1-ethenediamine To a solution of N-[2-[[5-(1,3-dioxolan-2-yl)-2-furanylmethyl]thio]ethyl]-N'-methyl-2-nitro-1,1-ethenediamine (1.65 g) and dimethylamine hydrochloride (16.3 g) in water (3.75 ml) and dioxan (6.2 ml) was added 2 N hydrochloric acid (3.75 ml) and the solution kept at room temperature for 25 min. A solution of dimethylamine in water (40%) (0.9 ml) was added followed by a solution of sodium cyanoborohydride (0.3 g) in water (1 ml). After 3 h, the clear aqueous solution was separated from the oily residue and evaporated in vacuo. Water (20 ml) was added to the syrupy residue and the aqueous solution separated from the insoluble oil. To the aqueous solution was added acetic acid (2 ml) and after 30 min. anhydrous sodium carbonate (22 g) was added. The solution was evaporated in vacuo and to the residue was added tetrahydrofuran (120 ml) and an excess of sodium carbonate. After 15h, the mixture was filtered, the filtrate evaporated in vacuo to give an oil which was dissolved in acetone (50 ml), the solution treated with decolourising characal, boiled and filtered. The filtrate was evaporated in vacuo to give a dark oil (0.77 g) which was chromatograhed on silica using methanol-0.88 ammonia (79:1) to give an oil (0.17 g) which was dissolved in methyl isobutyl ketone. The solid which separated was crystallised from isopropyl acetate to give the title compound (0.015 g) m.p. 69°–71° which was not depressed on admixture with a sample prepared according to the method of Example 15 in British Patent Specification No. 1,565,966. The crystallisation liquors were evaporated to dryness in vacuo to give a viscous oil also consisting of the title compound (0.08 g). The nmr of this sample matched that quoted for the oily product obtained in Example 4.

If desired the furan derivative of formula (I) once obtained may be converted into an acid addition salt e.g. a hydrochloride using conventional methods. Thus for example appropriate quantities of the free base of formula (I) and an acid (e.g. hydrochloric acid) may be mixed in a suitable solvent(s) e.g. an alcohol such as ethanol or an ester such as ethyl acetate.

We claim:

1. A process for the preparation of ranitidine of formula (I)

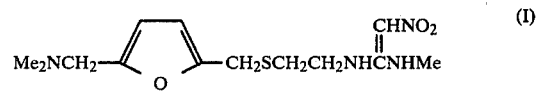

which comprises treating an aldehyde of formula (II)

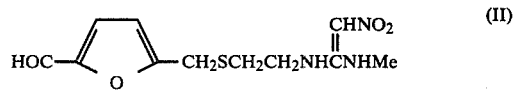

with dimethylamine and a reducing agent which is capable of effecting reductive alkylation to introduce the dimethylaminomethyl group but which does not reduce the nitroethene group, the reaction being carried out in a suitable solvent.

2. A process as claimed in claim 1 wherein said solvent is selected from the group consisting of aqueous alkanols, aqueous dioxan and aqueous tetrahydrofuran.

3. A process as claimed in claim 1, wherein said reducing agent is selected from the group consisting of diborane, aluminium hydride and alkali and alkaline earth metal borohydrides.

4. A process as claimed in claim 3 wherein said reducing agent is sodium borohydride or sodium cyanoborohydride.

5. A process as claimed in claim 4 wherein reduction is effected in the presence of an acid or the reaction with the reducing agent is followed by treatment with an acid.

6. A process as claimed in claim 1 carried out at a temperature of from 10° to 100° C.

7. A process as claimed in claim 1, wherein said aldehyde of formula (II) is generated in situ from an acetal of formula (III)

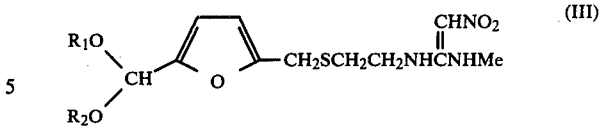

in which $R_1$ and $R_2$ are both alkyl groups or the group $R_1OCHOR_2$ forms a cyclic acetal.

8. A process as claimed in claim 7, wherein an acetal of formula (III) in which the group $R_1OCHOR_2$ is a 1,3-dioxolan-2-yl group is hydrolysed using an inorganic or an organic acid to form said aldehyde of formula (II) in the presence of an excess of dimethylamine hydrochloride.

9. A process as claimed in claim 1 in which said compound of formula (I) is converted into an acid addition salt.

10. A process as claimed in claim 9 in which said acid addition salt is the hydrochloride.

* * * * *